US011350963B2

(12) United States Patent
Aljuri et al.

(10) Patent No.: US 11,350,963 B2
(45) Date of Patent: Jun. 7, 2022

(54) FLUID JET TISSUE ABLATION APPARATUS

(71) Applicant: PROCEPT BioRobotics Corporation, Redwood Shores, CA (US)

(72) Inventors: Nikolai Aljuri, Hillsborough, CA (US); Edward Karpman, Los Altos, CA (US); Chris Danek, San Carlos, CA (US)

(73) Assignee: PROCEPT BioRobotics Corporation, Redwood City, CA (US)

( * ) Notice: Subject to any disclaimer, the term of this patent is extended or adjusted under 35 U.S.C. 154(b) by 264 days.

(21) Appl. No.: 16/555,019

(22) Filed: Aug. 29, 2019

(65) Prior Publication Data

US 2019/0380730 A1 Dec. 19, 2019

Related U.S. Application Data

(60) Division of application No. 15/388,515, filed on Dec. 22, 2016, now Pat. No. 10,448,966, which is a
(Continued)

(51) Int. Cl.
*A61B 17/3203* (2006.01)
*A61B 17/00* (2006.01)
*A61B 18/00* (2006.01)

(52) U.S. Cl.
CPC ............ *A61B 17/3203* (2013.01); *A61B 2017/00154* (2013.01); *A61B 2017/00172* (2013.01);
(Continued)

(58) Field of Classification Search
CPC .......... A61B 17/3203; A61B 17/32037; A61B 2017/00154; A61B 2017/00172;
(Continued)

(56) References Cited

U.S. PATENT DOCUMENTS

| 3,818,913 A | 6/1974 | Wallach |
| 3,821,510 A | 6/1974 | Muncheryan |

(Continued)

FOREIGN PATENT DOCUMENTS

| CN | 101460101 A | 6/2009 |
| CN | 102271595 A | 12/2011 |

(Continued)

OTHER PUBLICATIONS

Nishimura et al., Similarity Law on Shedding Frequency of Cavitation Cloud Induced by a Cavitating Jet, 2012, Journal of Fluid Science and Technology, vol. 7, No. 3, pp. 405-420. (Year: 2012).*
(Continued)

*Primary Examiner* — Jocelin C Tanner
(74) *Attorney, Agent, or Firm* — FisherBroyles LLP; John Shimmick

(57) ABSTRACT

An apparatus is configured to provide hemostasis with tissue removal in order to inhibit one or more of blood loss or tissue drainage. In many embodiments, a nozzle releases a liquid jet in a liquid medium in order to provide cavitation and a plurality of shedding pulses. The liquid jet, its cavitation and the plurality of shedding pulses can affect vascular tissue in order to promote clotting in order to inhibit bleeding. In many embodiments, vessels of the vascular tissue are affected at a distance from a region where cavitation of the water jet contacts the tissue. In many embodiments, the cavitation and plurality of shedding pules are related to a pulsatile shear wave propagating along the blood vessel that is related to clot promoting changes of the blood vessel.

14 Claims, 9 Drawing Sheets

Related U.S. Application Data continuation of application No. PCT/US2015/038605, filed on Jun. 30, 2015.

(60) Provisional application No. 62/032,958, filed on Aug. 4, 2014, provisional application No. 62/019,299, filed on Jun. 30, 2014.

(52) U.S. Cl.
CPC .......... *A61B 2017/00274* (2013.01); *A61B 2017/32032* (2013.01); *A61B 2017/32035* (2013.01); *A61B 2018/00547* (2013.01)

(58) Field of Classification Search
CPC .......... A61B 2017/00274; A61B 2017/32032; A61B 2017/32035; A61B 2018/00547
See application file for complete search history.

(56) References Cited

U.S. PATENT DOCUMENTS

| | | |
|---|---|---|
| 3,847,988 A | 11/1974 | Gold |
| 3,875,229 A | 4/1975 | Gold |
| 4,097,578 A | 6/1978 | Perronnet |
| 4,220,735 A | 9/1980 | Dieck |
| 4,239,776 A | 12/1980 | Bayles |
| 4,377,584 A | 3/1983 | Rasmusson |
| 4,386,080 A | 5/1983 | Crossley |
| 4,461,283 A | 7/1984 | Doi |
| 4,474,251 A | 10/1984 | Johnson, Jr. |
| 4,560,373 A | 12/1985 | Sugino |
| 4,636,505 A | 1/1987 | Tucker |
| 4,672,963 A | 6/1987 | Barken |
| 4,760,071 A | 7/1988 | Rasmusson |
| 4,776,349 A | 10/1988 | Nashef |
| 4,913,698 A | 4/1990 | Ito |
| 5,037,431 A | 8/1991 | Summers |
| 5,116,615 A | 5/1992 | Gokcen |
| 5,135,482 A | 8/1992 | Neracher |
| 5,207,672 A | 5/1993 | Roth |
| 5,257,991 A | 11/1993 | Fletcher |
| 5,267,341 A | 11/1993 | Shearin |
| 5,269,785 A | 12/1993 | Bonutti |
| 5,322,503 A | 6/1994 | Desai |
| 5,322,504 A | 6/1994 | Doherty |
| 5,454,782 A | 10/1995 | Perkins |
| 5,496,267 A | 3/1996 | Drasler |
| 5,505,729 A | 4/1996 | Rau |
| 5,514,669 A | 5/1996 | Selman |
| 5,527,330 A | 6/1996 | Tovey |
| 5,558,634 A | 9/1996 | Mitchell |
| 5,562,703 A | 10/1996 | Desai |
| 5,620,414 A | 4/1997 | Campbell, Jr. |
| 5,630,794 A | 5/1997 | Lax |
| 5,649,923 A | 7/1997 | Gregory |
| 5,672,153 A | 9/1997 | Lax |
| 5,672,171 A | 9/1997 | Andrus |
| 5,753,641 A | 5/1998 | Gormley |
| 5,770,603 A | 6/1998 | Gibson |
| 5,772,657 A | 6/1998 | Hmelar |
| 5,773,791 A | 6/1998 | Kuykendal |
| 5,782,848 A | 7/1998 | Lennox |
| 5,785,521 A | 7/1998 | Rizoiu |
| 5,817,649 A | 10/1998 | Labrie |
| 5,833,701 A | 11/1998 | Gordon |
| 5,836,941 A | 11/1998 | Yoshihara |
| 5,861,002 A | 1/1999 | Desai |
| 5,871,462 A * | 2/1999 | Yoder ............... A61B 17/1644 604/22 |
| 5,872,150 A | 2/1999 | Elbrecht |
| 5,902,499 A | 5/1999 | Richerzhagen |
| 5,964,775 A * | 10/1999 | Gordon ............... A61F 9/013 128/898 |
| 5,994,362 A | 11/1999 | Gormley |
| 6,022,860 A | 2/2000 | Engel |
| 6,066,130 A | 5/2000 | Gregory |
| 6,071,284 A | 6/2000 | Fox |
| 6,117,128 A | 9/2000 | Gregory |
| 6,142,991 A | 11/2000 | Schatzberger |
| 6,179,831 B1 | 1/2001 | Bliweis |
| 6,200,573 B1 | 3/2001 | Locke |
| 6,217,543 B1 | 4/2001 | Anis |
| 6,217,860 B1 | 4/2001 | Woo |
| 6,228,046 B1 | 5/2001 | Brisken |
| 6,231,591 B1 | 5/2001 | Desai |
| 6,254,597 B1 | 7/2001 | Rizoiu |
| 6,296,639 B1 | 10/2001 | Truckai |
| 6,375,635 B1 | 4/2002 | Moutafis |
| 6,378,525 B1 | 4/2002 | Beyar |
| 6,413,256 B1 | 7/2002 | Truckai |
| 6,425,877 B1 | 7/2002 | Edwards |
| 6,440,105 B1 | 8/2002 | Menne |
| 6,451,017 B1 | 9/2002 | Moutafis |
| 6,565,555 B1 | 5/2003 | Ryan |
| 6,572,578 B1 | 6/2003 | Blanchard |
| 6,607,524 B1 | 8/2003 | LaBudde |
| 6,720,745 B2 | 4/2004 | Lys |
| 6,814,731 B2 | 11/2004 | Swanson |
| 6,821,275 B2 | 11/2004 | Truckai |
| 6,890,332 B2 | 5/2005 | Truckai |
| 6,913,605 B2 * | 7/2005 | Fletcher ............... A61B 17/3203 606/13 |
| 6,953,461 B2 | 10/2005 | McClurken |
| 6,960,182 B2 | 11/2005 | Moutafis |
| 6,986,764 B2 | 1/2006 | Davenport |
| 7,008,421 B2 | 3/2006 | Daniel |
| 7,015,253 B2 | 3/2006 | Escandon |
| 7,115,100 B2 | 10/2006 | McRury |
| 7,122,017 B2 | 10/2006 | Moutafis |
| 7,163,875 B2 | 1/2007 | Richerzhagen |
| 7,326,054 B2 | 2/2008 | Todd |
| 7,882,841 B2 | 2/2011 | Aljuri |
| 8,092,507 B2 | 1/2012 | Tomasello |
| 8,795,194 B2 | 8/2014 | Howard |
| 8,814,921 B2 | 8/2014 | Aljuri |
| 9,232,959 B2 | 1/2016 | Aljuri |
| 9,232,960 B2 | 1/2016 | Aljuri |
| 9,237,902 B2 | 1/2016 | Aljuri |
| 9,364,250 B2 | 6/2016 | Aljuri |
| 9,364,251 B2 | 6/2016 | Aljuri |
| 9,510,853 B2 | 12/2016 | Aljuri |
| 9,668,764 B2 | 6/2017 | Aljuri |
| 9,848,904 B2 | 12/2017 | Aljuri |
| 9,867,635 B2 | 1/2018 | Alvarez |
| 9,931,445 B2 | 4/2018 | Pustilnik |
| 10,448,966 B2 | 10/2019 | Aljuri |
| 2001/0002562 A1 | 6/2001 | Moutafis |
| 2001/0048942 A1 | 12/2001 | Weisman |
| 2002/0010502 A1 | 1/2002 | Trachtenberg |
| 2002/0022869 A1 | 2/2002 | Hareyama |
| 2002/0040220 A1 | 4/2002 | Zvuloni |
| 2002/0045911 A1 | 4/2002 | Fletcher |
| 2002/0111617 A1 | 8/2002 | Cosman |
| 2002/0128637 A1 | 9/2002 | von der Heide |
| 2003/0036768 A1 | 2/2003 | Hutchins |
| 2003/0060819 A1 | 3/2003 | McGovern |
| 2003/0065321 A1 | 4/2003 | Carmel |
| 2003/0073902 A1 | 4/2003 | Hauschild |
| 2003/0135205 A1 | 7/2003 | Davenport |
| 2003/0139041 A1 | 7/2003 | LeClair |
| 2003/0216722 A1 | 11/2003 | Swanson |
| 2004/0097829 A1 | 5/2004 | McRury |
| 2004/0133254 A1 | 7/2004 | Sterzer |
| 2004/0143269 A1 | 7/2004 | Pude |
| 2005/0004516 A1 | 1/2005 | Vanney |
| 2005/0256517 A1 | 11/2005 | Boutoussov |
| 2006/0030787 A1 | 2/2006 | Quay |
| 2006/0089626 A1 | 4/2006 | Vlegele |
| 2006/0149193 A1 | 7/2006 | Hall |
| 2006/0229550 A1 * | 10/2006 | Staid ............... A61B 17/3203 604/27 |
| 2007/0230757 A1 | 10/2007 | Trachtenberg |
| 2008/0178654 A1 | 7/2008 | Hochmitz |
| 2008/0253527 A1 | 10/2008 | Boyden |

(56) References Cited

U.S. PATENT DOCUMENTS

| | | |
|---|---|---|
| 2009/0018533 A1 | 1/2009 | Perkins |
| 2009/0088775 A1 | 4/2009 | Swarup |
| 2009/0227998 A1 | 9/2009 | Aljuri |
| 2010/0076269 A1 | 3/2010 | Makower |
| 2010/0145254 A1 | 6/2010 | Shadduck |
| 2010/0179522 A1 | 7/2010 | Companion |
| 2010/0179528 A1 | 7/2010 | Shadduck |
| 2011/0005288 A1* | 1/2011 | Matsui ............... C21D 11/00 72/56 |
| 2011/0104800 A1 | 5/2011 | Kensy |
| 2011/0117517 A1* | 5/2011 | Bergheim ............. A61C 5/62 433/81 |
| 2011/0184291 A1 | 7/2011 | Okamura |
| 2011/0184391 A1 | 7/2011 | Aljuri |
| 2011/0208224 A1 | 8/2011 | Kojima |
| 2012/0065656 A1 | 3/2012 | Karwei |
| 2012/0157841 A1 | 6/2012 | Glaenzer |
| 2013/0158534 A1 | 6/2013 | Hoey |
| 2013/0253484 A1 | 9/2013 | Aljuri |
| 2013/0253488 A1 | 9/2013 | Aljuri |
| 2013/0261540 A1 | 10/2013 | Crank |
| 2013/0267889 A1 | 10/2013 | Aljuri |
| 2014/0058361 A1 | 2/2014 | Gordon |
| 2014/0193833 A1 | 7/2014 | Srivastava |
| 2014/0309649 A1 | 10/2014 | Alvarez |
| 2015/0025539 A1 | 1/2015 | Alvarez |
| 2015/0045777 A1 | 2/2015 | Aljuri |
| 2015/0057646 A1 | 2/2015 | Aljuri |
| 2015/0088107 A1 | 3/2015 | Aljuri |
| 2015/0088110 A1 | 3/2015 | Aljuri |
| 2015/0313666 A1 | 11/2015 | Aljuri |
| 2015/0335344 A1 | 11/2015 | Aljuri |
| 2016/0074059 A1 | 3/2016 | Aljuri |
| 2016/0143778 A1 | 5/2016 | Aljuri |
| 2016/0228141 A1 | 8/2016 | Aljuri |
| 2017/0172548 A1 | 6/2017 | Aljuri |
| 2017/0172668 A1 | 6/2017 | Aljuri |
| 2017/0231655 A1 | 8/2017 | Aljuri |
| 2018/0263647 A1 | 9/2018 | Aljuri |

FOREIGN PATENT DOCUMENTS

| | | |
|---|---|---|
| CN | 102271602 | 12/2011 |
| CN | 103118611 | 5/2013 |
| CN | 103764056 | 4/2014 |
| EP | 1075853 A2 | 2/2001 |
| EP | 3188667 A1 | 7/2017 |
| JP | 2001046528 A | 2/2001 |
| JP | 2007020837 A | 2/2007 |
| JP | 2012508068 A | 4/2012 |
| JP | 2012523253 A | 10/2012 |
| JP | 2013518684 A | 5/2013 |
| WO | 03088833 A1 | 10/2003 |
| WO | 2004028592 A1 | 4/2004 |
| WO | 2004080529 A2 | 9/2004 |
| WO | 2006089426 A1 | 8/2006 |
| WO | 2007101015 A1 | 9/2007 |
| WO | 2007114917 A2 | 10/2007 |
| WO | 2008083407 | 7/2008 |
| WO | 2008083407 A1 | 7/2008 |
| WO | 2009029461 A1 | 3/2009 |
| WO | 2009111736 | 9/2009 |
| WO | 2009111736 A1 | 9/2009 |
| WO | 2009152613 A1 | 12/2009 |
| WO | 2010054220 A1 | 5/2010 |
| WO | 2010144419 A2 | 12/2010 |
| WO | 2011097505 | 8/2011 |
| WO | 2011097505 A1 | 8/2011 |
| WO | 2011100753 A2 | 8/2011 |
| WO | 2011141775 A1 | 11/2011 |
| WO | 2013129657 A1 | 9/2013 |
| WO | 2013130895 | 9/2013 |
| WO | 2013130895 A1 | 9/2013 |
| WO | 2014127242 | 8/2014 |
| WO | 2014127242 A2 | 8/2014 |
| WO | 2014165703 | 10/2014 |
| WO | 2015035249 A2 | 3/2015 |
| WO | 2015200538 A1 | 12/2015 |
| WO | 2016004071 A1 | 1/2016 |
| WO | 2016037132 A1 | 3/2016 |
| WO | 2016037137 | 3/2016 |

OTHER PUBLICATIONS

Botto et al., "Electrovaporization of the Prostate with the Gyrus Device," J. Endourol. (Apr. 2001) 15(3):313-316.

European Search Report dated Dec. 11, 2017 for European Patent Application No. 15815102.7.

Hillegersberg et al., "Water-jet-cooled Nd:YAG laser coagulation: selective destruction of rat liver metastases," Lasers Surg Med. 1991; 11(5):445-454. [Abstract Only].

International Search Report dated Oct. 1, 2015 for International Patent Application No. PCT/US2015/038605.

Jian, et al. The Development of the Water Jet Scalpel With Air Pressure. Trans. ASME (Jun. 2001) 123(2):246-248.

Nishimura, et al. Similarity Law on Shedding Frequency of Cavitation Cloud Induced by a Cavitating Jet. Journal of Fluid Science and Technology, vol. 7, No. 3, 2012, pp. 405-420.

Prajapati, et al., Pluripotent Stem Cell within the Prostate could be Responsible for Benign Prostate Hyperplasia in Human, J Stem Cell Res Ther2014, 4:1.

Prajapati, et al., Prostate Stem Cells in the Development of Benign Prostate Hyperplasia and Prostate Cancer: Emerging Role and Concepts, Biomed Res Int 2013; 2013:107954.

Richerzhagen et al., "Water Jet Guided Laser Cutting: a Powerful Hybrid Technology for Fine Cutting and Grooving," Proceedings of the 2004 Advanced Laser Applications Conference and Exposition, Ann Arbor, Michigan, Sep. 20-22, 2004, ALAC 2004, 2:175-182; retrieved from the internet <http://www.synova.ch/pdf/ALAC04.pdf>.

Ruggeri, et al., Activation-independent platelet adhesion and aggregation under elevated shear stress. Blood. Sep. 15, 2006; 108(6):1903-1910.

Sander et al., "The waterjet-guided Nd:YAG laser in the treatment of gastroduodenal ulcer with a visible vessel. A randomized controlled and prospective study," Endoscopy. Sep. 1989; 21(5):217-220. [Abstract Only].

Sander et al., "Waterjet guided Nd:YAG laser coagulation-its application in the field of gastroenterology," Endosc Surg Allied Technol. Aug. 1993; 1(4):233-238. [Abstract Only].

Staider et al., "Repetitive Plasma Discharges in Saline Solutions," Appl. Phys. Lett. (Dec. 2001), 79(27):4503-4505.

Woloszko et al., "Plasma Characteristics of Repetitively-Pulsed Electrical Discharges in Saline Solutions Used for Surgical Procedures," (2002) IEEE Trans. Plasma Sci. 30(3):1376-1383.

Wright, et al. Cavitation of a submerged jet. Exp Fluids (2013) 54:1541.

* cited by examiner

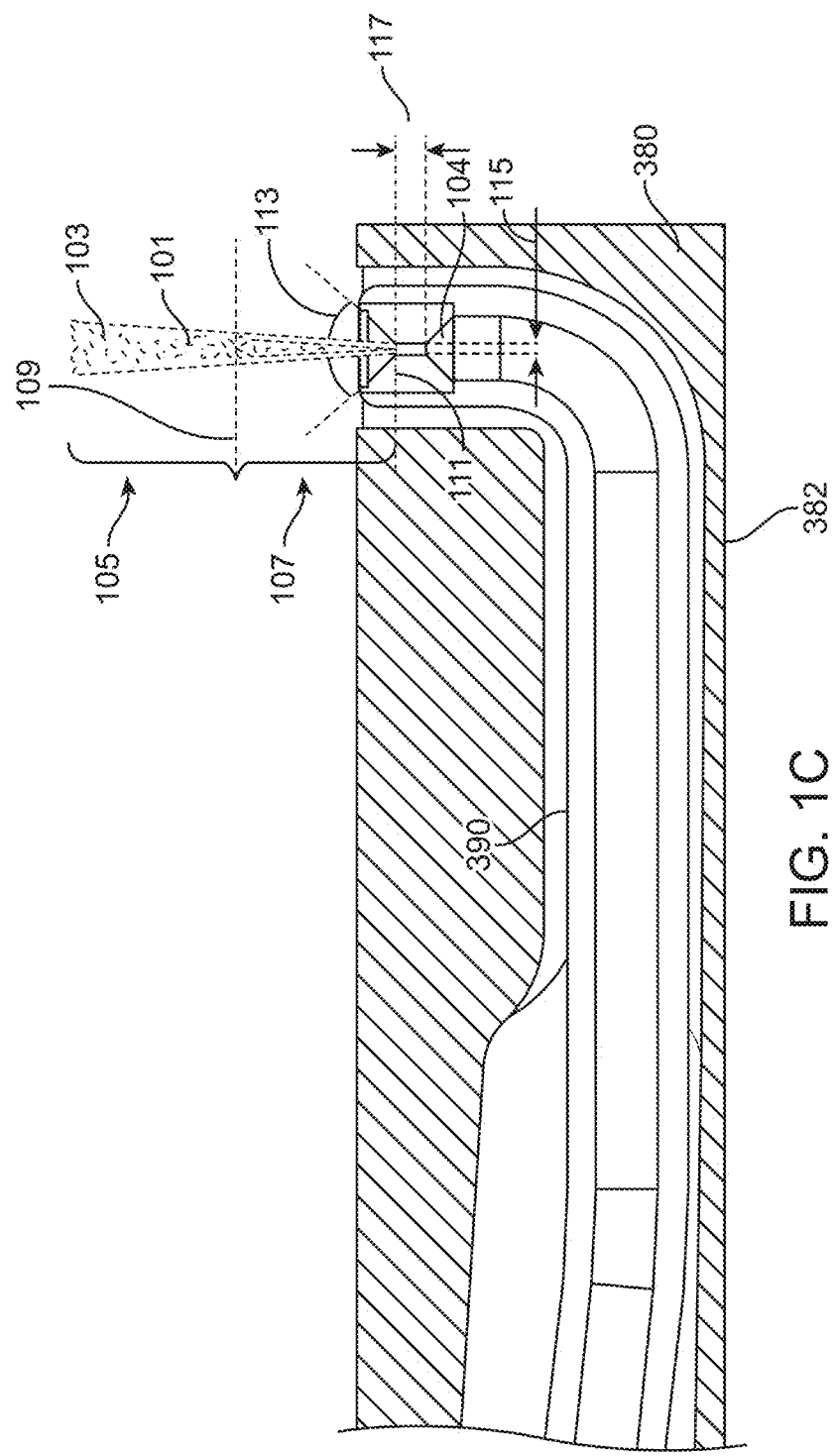

FLUID JET TISSUE ABLATION APPARATUS

RELATED APPLICATIONS

The present application is a divisional of U.S. patent application Ser. No. 15/388,515, filed Dec. 22, 2016, now U.S. Pat. No. 10,448,996, isued Oct. 22, 2019, which is a continuation of International Application No. PCT/US2015/038605, filed Jun. 30, 2015, published as WO 2016/004071 on Jan. 7, 2016, which claims priority to U.S. Provisional Application No. 62/019,299, filed Jun. 30, 2014, and U.S. Provisional Application No. 62/032,958, filed Aug. 4, 2014, the entire disclosures of which are incorporated herein by reference.

The subject matter of this international application is related to and incorporates by references the complete disclosures of the following U.S. patents and applications: U.S. Provisional Application No. 61/874,849, filed Sep. 6, 2013, entitled "AUTOMATED IMAGE-GUIDED TISSUE RESECTION AND TREATMENT," U.S. Provisional Application No. 61/972,730, filed Mar. 31, 2014, entitled "AUTOMATED IMAGE-GUIDED TISSUE RESECTION AND TREATMENT," U.S. Provisional Application No. 62/019,305, filed Jun. 30, 2014, entitled "AUTOMATED IMAGE-GUIDED TISSUE RESECTION AND TREATMENT," U.S. patent application Ser. No. 12/700,568, filed Feb. 4, 2010, entitled "MULTI FLUID TISSUE RESECTION METHODS AND DEVICES," now U.S. Pat. No. 9,232,959, issued Jan. 12, 2016.

The subject matter of this international application is also related to International Application No. PCT/US2013/028441, filed Feb. 28, 2013, published as WO 2013/130895 on Sep. 6, 2013, entitled "AUTOMATED IMAGE-GUIDED TISSUE RESECTION AND TREATMENT," and International Application No. PCT/US2011/023781, filed Feb. 4, 2011, published as WO 2011/097505 on Nov. 8, 2011, entitled "MULTI FLUID TISSUE RESECTION METHODS AND DEVICES," the entire disclosures of which are incorporated herein by reference.

BACKGROUND

The field of the present invention is related to the treatment of tissue, and more specifically to the surgical treatment of an organ such as the prostate.

Prior methods and apparatus of incising tissue of subjects such as patients can result in less than ideal results in at least some instances. For example, prior methods of prostate surgery can result in longer healing time and less than ideal outcomes in at least some instances. In at least some instances, prior methods and apparatus of tissue resection can result in more bleeding than would be ideal. Also, the prior methods and apparatus of cutting tissue can provide less accurate cuts than would be ideal. Although electrocautery and laser coagulation have been proposed as a potential solution to bleeding, treatment with electrocautery or laser coagulation may result in an additional step to removal of tissue, and the control of bleeding can be less than ideal. Also, the heat associated with electrocautery may result in less than ideal results in at least some instances.

With prior surgical procedures, the recovery time of the patient can be related to the manner in which tissue is removed, and it would be helpful to provide surgical procedures with decreased recovery times. Also, tissue drainage can be somewhat greater than would be ideal and can be related to the manner in which tissue is incised. In at least some instances, patients may benefit from a blood transfusion following surgery, and it would be better if fewer blood transfusions were required subsequent to surgery.

Although removal of tissue with water jets can result in successful removal of tissue, work in relation to embodiments suggests that further improvements may be helpful. For example, the prior methods and apparatus of cutting tissue with a water jet can result in somewhat less accurate cutting and potentially more bleeding than would be ideal in at least some instances. Although prior methods of tissue cutting can cut ablate tissue with fluid jet technology with the decreased transfer of heat to the tissue, work in relation to embodiments suggests that in at least some instances prior water jet cutting can result in amounts of bleeding that can be somewhat greater than would be ideal.

In light of the above, it would be helpful to provide improved methods and apparatus for tissue treatment such as surgery. Ideally such methods would provide improved resection of tissue with decreased bleeding and improved outcomes.

SUMMARY

The embodiments provide improved methods and apparatus of cutting tissue with a water jet. In many embodiments, the apparatus is configured to provide hemostasis with tissue removal in order to inhibit one or more of blood loss or tissue drainage. In many embodiments, a nozzle releases a liquid jet in a liquid medium in order to provide cavitation and a plurality of shedding pulses. The cavitation and the plurality of shedding pulses can affect vascular tissue in order to promote clotting in order to inhibit bleeding. In many embodiments, vessels of the vascular tissue are affected at a distance from a region where cavitation of the water jet contacts the tissue. In many embodiments, the cavitation and plurality of shedding pules are related to a pulsatile shear wave propagating along the blood vessel that is related to clot promoting changes of the blood vessel. In many embodiments, the nozzle is placed at a distance from a tissue removal profile in order to provide substantially abrasive tissue removal, in which vascular tissue and non-vascular tissue with less collagen are removed at similar rates. Alternatively or in combination, the nozzle can be placed at a distance from a tissue removal profile in order to provide substantially selective tissue removal, in which vascular tissue and non-vascular tissue with less collagen are removed at substantially different rates. In many embodiments, an endothelial cell lining of the vessel wall is affected in order to promote blood clotting within the vessel.

In many embodiments wherein bleeding of the vascular tissue is inhibited with one or more of: induced thrombosis in capillaries and arterioles related to endothelial injury, shear stress and reduction in blood flow; adhesion and aggregation of platelets; deposition of fibrin; deposition of fibrin related to obstructive vessel clotting; fluid pressure in an affected zone; fluid pressure in an affected zone at a distance from a removal profile; inhibited blood the affected vessels; partial collapse of the affected blood vessels; full collapse of the affected blood vessels; and combinations thereof.

INCORPORATION BY REFERENCE

All patents, applications, and publications referred to and identified herein are hereby incorporated by reference in their entirety, and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which:

FIG. 1C shows a nozzle for treating tissue in accordance with embodiments;

DETAILED DESCRIPTION

Figure 1A:
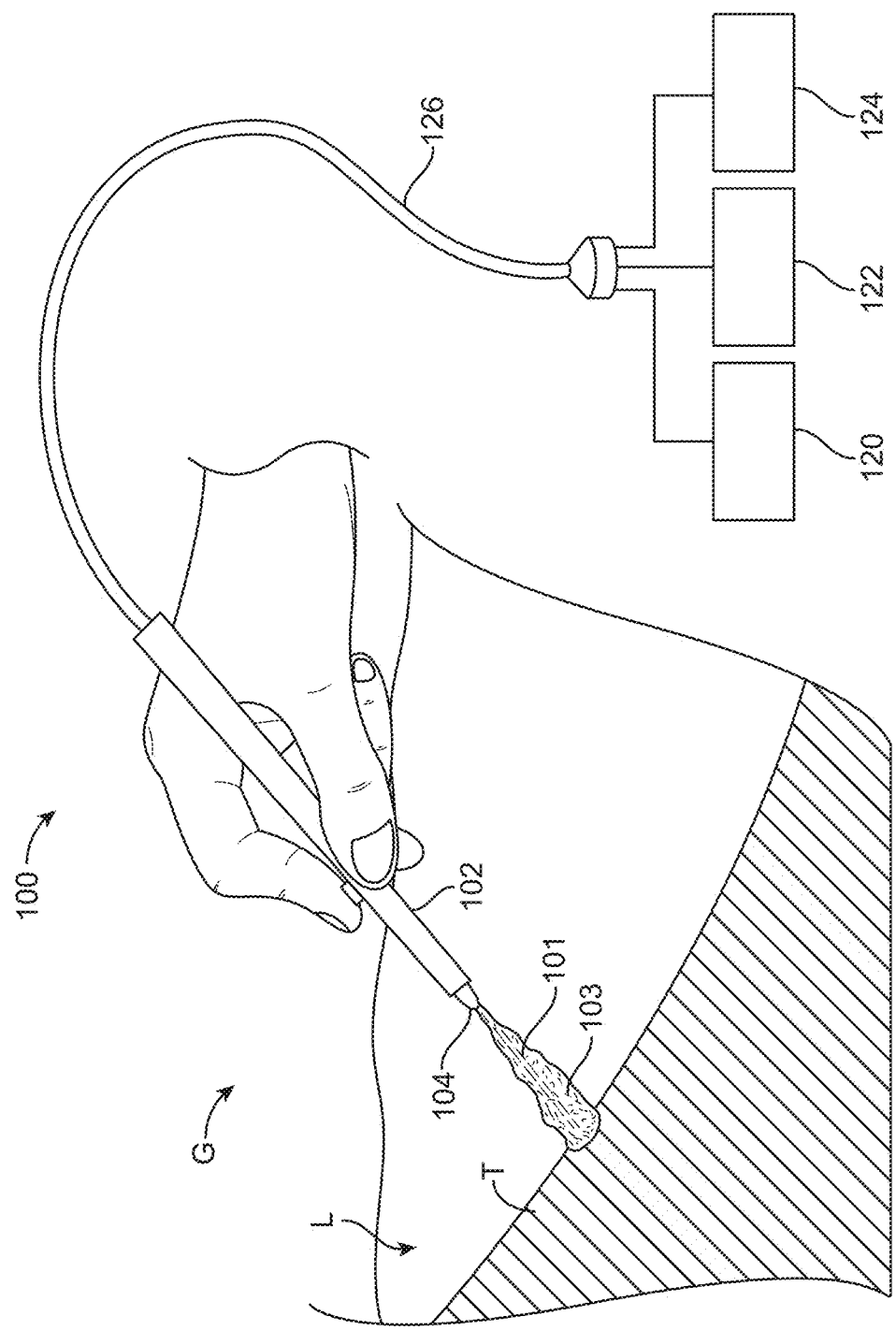
FIG. 1A is a schematic illustration of a device suitable for treating tissue in accordance with embodiments.

A better understanding of the features and advantages of the present disclosure will be obtained by reference to the following detailed description that sets forth illustrative embodiments, in which the principles of embodiments of the invention are utilized, and the accompanying drawings.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as described herein.

As used herein the term "AquaBeam" encompasses a liquid jet provided in a liquid to provide cavitation to tissue.

The fluid jet tissue ablation (hereinafter "Aquablation") and methods and apparatus for providing hemostasis with tissue cutting as disclosed herein are well suited for combination with many prior surgical procedures and apparatus. In many embodiments, improved hemostasis is provided, which is related to the tissue incision with the jet. In many embodiments, the jet comprises jet in a liquid medium which induces cavitation of the jet, which can be referred to as a cool flame, which can be related to the substantially mechanical shear stress interactions between the high-velocity fluid jet and the vessels in contact with the jet. In many embodiments, the jet comprises sufficient energy above the threshold of cavitation such that tissue removal of the jet is substantially insensitive to the type of tissue and amount of collagen of the tissue and can cut vascular and granular tissue at similar rates. The mechanical contact of tissue with the jet and corresponding shear can induce micro-thrombosis in capillaries and arterioles can provide improved coagulation and corresponding hemostasis. In many embodiments, the endothelial cells can be affected so as to facilitate the release of blood clotting factors. The effect to the endothelial cells as described herein can occur at a distance from the site where the cavitations of the jet and liquid medium strike the tissue in order to provide improved hemostasis. In many embodiments, the substantially mechanical shear stress can provide damage to the endothelial cells and provide a reduction in blood flow, and may facilitate and enhance the adhesion and aggregation of platelets and deposition of fibrin, so as to provide obstructive vessel clotting.

In many embodiments, shear stress supplied by the jet is sufficient to induce platelet aggregation independent of complement activation. The platelet aggregation independent of complement activation can occur in a manner similar to areas of high hemodynamic shear, such as in arterial stenosis as described previously. See Blood. Sep. 15, 2006; 108(6): 1903-1910. PMCID: PMC1895550 Activation-independent platelet adhesion and aggregation under elevated shear stress. Z M Rugerri et al. By providing water jet shear stress directly to affected vessels, for a sufficient period of time platelet aggregation may achieve initial hemostasis, allowing the coagulation cascade to thrombose the affected vessels and achieve lasting hemostasis. As shear increases, the time to achieve hemostatic platelet aggregation may decrease. The Aquablation as described herein can be tuned to improve hemostasis by controlling pump power (and with it fluid velocity, and shear stress magnitude) and rate of translation of the water jet. In many embodiments, higher pumping power and slower translation of the jet are prohemostatic. Alternatively or in combination, the relative contribution of various hemostatic factors (local pressure gradients, shear modulated hemostasis, cavitation induced thrombosis) can vary depending on the position of the vessel relative to the jet (for a specific pump power) position, as related to the evolution of the flame with distance traveled from the jet nozzle exit.

While the vessel clotting can be provided in one or more of many ways, in many embodiments the fluid pressure in the affected zone during tissue treatment with the water jet may rapidly inhibit and substantially decrease blood from exiting the affected vessels. In many embodiments, the hemostasis as described herein is related to the partial or full collapse of the affected vessels. In many embodiments, the substantially mechanical shear stress provided with the cavitations can provides fluid jet tissue resection and ablation of tissue and also to heat-free tissue coagulation.

FIG. 1A shows apparatus 100 comprising a handheld device, which may comprise a shaft 102 having a distal end with a nozzle 104 oriented to deliver a pressurized fluid in an axial stream water jet 101 with cavitation 103 as disclosed herein. The jet and tissue T can be immersed in a liquid L such as saline or another liquid to provide shedding pulses with cavitation as disclosed herein, for example. The liquid can be provided over the tissue with a gas G such as air above the liquid. Alternatively or in combination, the tissue may comprise an internal tissue covered with the liquid, for example. Water or other fluid is delivered under pressure from the nozzle. The handheld device 100 is capable of delivering an axial water jet or other pressurized fluid stream and is useful for the manual cutting of tissue or bone, for example. The handheld device 100 is connected to a pressurized fluid source 120, a fluid flow monitor 122, and control circuitry 124, typically by a connecting cord 126. The fluid flow monitor 122 may comprise a pressure monitor for example. The user can thus control the fluid pressure, movement of the nozzle (velocity, direction, limits, etc.) and other aspects of the treatment protocol in addition to the axial and rotational movement parameters using the control circuitry. Optionally, although not illustrated, the nozzle 104 will be adjustable in order to adjust the width and focus of the fluid stream FS in order to allow further flexibility for the treatment. When used for cutting tissue, the hand-held shaft can be manipulated much as a scalpel. Alternatively, the nozzle can be mounted on a computer-controlled positioning system such as a rotating, translating and oscillating probe, or a robotic arm, and combinations thereof.

In many embodiments, the pressurized pump comprises a high-pressure pump such as a piston pump, for example. The control circuitry can be coupled to the pressure monitor 122, so as to provide a controlled flow rate. The controlled flow rate, in combination with the nozzle can provide a cavitation flame at distance, in order to incise tissue as disclosed herein.

Figure 1B:
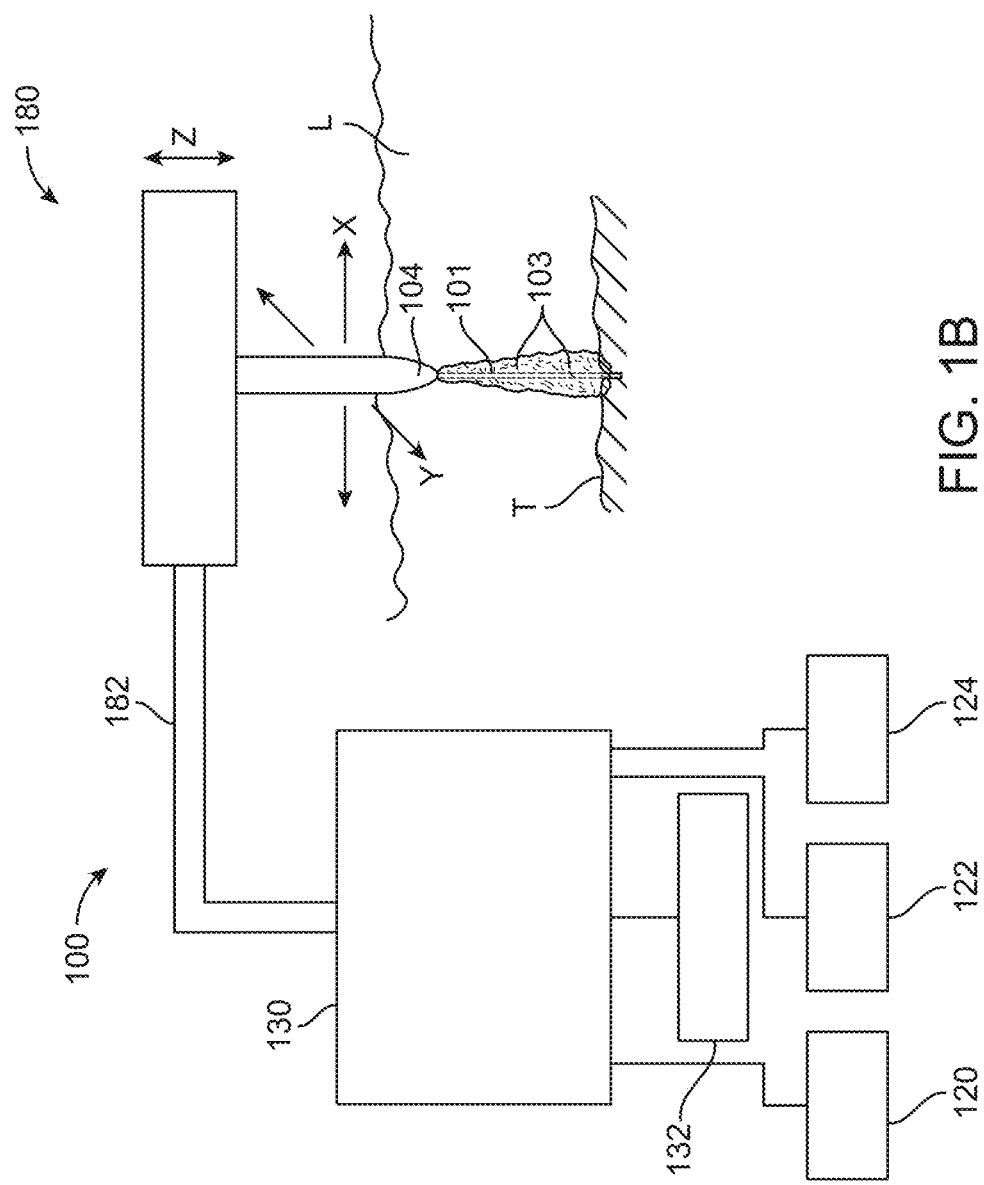
FIG. 1B shows a computer-controlled device suitable for treating tissue in accordance with embodiments.

FIG. 1B shows an apparatus 100 comprising computer-controlled device suitable for treating tissue T in accordance with embodiments. Apparatus 100 may comprise a linkage 130 coupled to the treatment probe in order to treat tissue in response to computer commands. The linkage may comprise a linkage capable of translation, or capable of a rotating, oscillating and translating, and combinations thereof, for example. The linkage can be coupled to the processor 132 and may be guided under user control, for example. The embodiments disclosed herein are suitable for combination with many devices to remove tissue, such as computer-controlled image guided treatment apparatus incorporated herein by reference elsewhere.

FIG. 1C shows a nozzle 104 for treating tissue in accordance with embodiments. The nozzle can be configured in one or more of many ways as described herein and is suitable for combination with flow rates in order to provide tissue removal with hemostasis as described herein. In many embodiments, a flow rate through the nozzle and the configuration of the nozzle provide a maximum tissue removal distance. The jet 101 from the nozzle may comprise a selective tissue removal region 105 and a non-selective tissue removal region 107. The selective tissue removal region 105 of the jet can selectively remove tissue at rates in response to collagen of the tissue. For example, collagenous tissue such as blood vessel walls can be removed more quickly than tissue with less collagen such as granular tissue. The non-selective tissue removal region 107 of the jet can remove tissue having different amounts of collagen as substantially similar rates. For example, collagenous tissue such as blood vessel walls can be removed at rates substantially similar to tissue with less collagen such as granular tissue. A threshold transition zone 109 can be located between the selective tissue removal region and the non-selective tissue removal region.

The nozzle can be mounted on a carrier 382 comprising a fluid delivery element and design considerations of the fluid delivery element. The carrier 382 can be provided on a rotating, translating and oscillating probe, for example. The jet orifice 111 design of the fluid delivery element can be configured in one or more of many ways as described herein, so as to provide a plurality of shedding pulses. Fluid jet ablation characteristics can be varied by varying the jet orifice geometry. For example, cone angle 113 variation can result in an increase or decrease in cavitation 103 occurring at the nozzle exit. The jet orifice design may comprise a cone at one or more of the entrance or the exit of the orifice 111. The cone angle can vary from 0 to 180 degrees, for example.

In many embodiments, the jet nozzle profile also influences the degree of fluid acceleration and amount of cavitation. For example, a sharp-edged orifice can induce a higher jet velocity at exit from the vena cava effect, with correspondingly greater amounts of cavitation 103 in the jet far field.

The orifice diameter 115 and orifice length 117 variation can result in a variation in nozzle back pressure and exit speed of the fluid stream. The resulting cavitation region varies with each of these parameters. The cavitation region may comprise a cloud of cavitation bubbles generated by the nozzle. The depth of tissue penetration can be determined and controlled as described herein. In many embodiments the cavitation region can be visualized with ultrasound imaging or optical imaging in combinations thereof. The cavitation region corresponds to a region where bubbles are formed, which allows the entrainment region to be visualized and can be referred to as a fluid flame. The cool cutting of the cavitation region can allow for tissue removal with minimal tissue damage. In many embodiments the cone angles within a range from about 40 degrees to about 80 degrees. A ratio of the orifice length to the inner diameter of the orifice can be within a range from about 1 to 10, for example, within a range from about 4 to 7. A person of ordinary skill in the art can design a jet orifice to treat tissue as described herein based on the teachings provided herein.

Cold Flame

Figure 2:
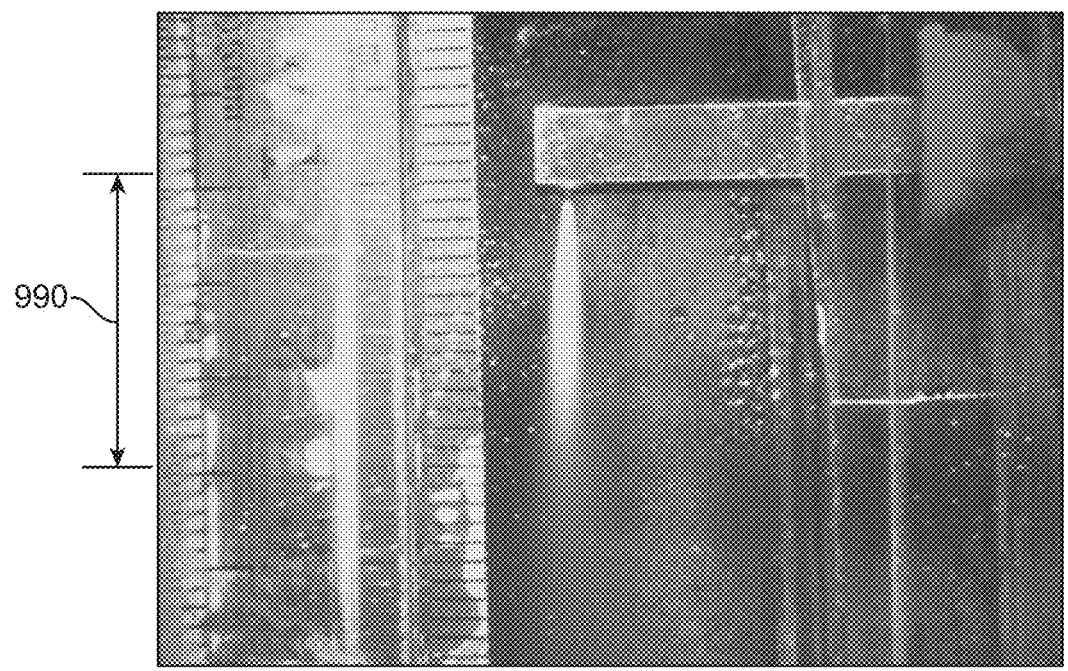
FIG. 2 shows an ablative flame visible to the human eye, in accordance with embodiments.

FIG. 2 shows an ablative flame visible to the human eye, in accordance with embodiments.

Figure 3:
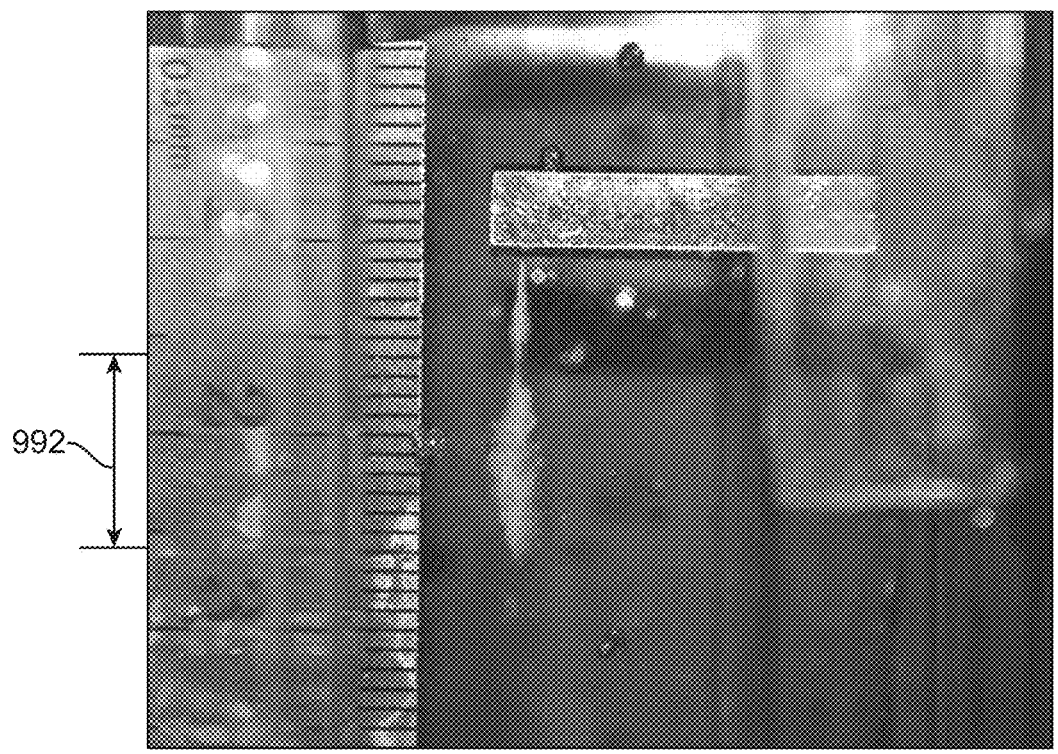
FIG. 3 shows a high-speed image of the ablative flame as in FIG. 2 taken at a speed of about 1/400 of a second, in accordance with embodiments.

FIG. 3 shows a high-speed image of the ablative flame as in FIG. 2. The image was taken at a speed of about 1/400 of a second.

The data of FIGS. 2 and 3 show that the ablative flame comprises a plurality of white clouds generated with the ablative stream when released from the nozzle. Work in relation to embodiments has shown that the cavitating cloud can shed from the jet at a characteristic shedding frequency. A length 992 of each cloud is related to the shedding frequency and the velocity of the cloud. The relatively cool ablative flame of the jet comprises a length 990 corresponding to the cutting length of the jet which can be adjusted to cut tissue to controlled depth as described herein. In many embodiments, nozzle of the jet is placed at least about a quarter of the length 992 of a shed cloud in an non-cutting configuration as shown in FIG. 3, in order to allow the shedding cloud to substantially form prior to the cloud striking tissue. This divergence of the shed cloud to a larger cross-sectional size can also provide improved tissue removal as the cloud can be distributed to a larger region of tissue and provide improved overlap among the pulses of the jet.

In addition to the impact pressure of the jet, the highly turbulent and aggressive region corresponding to the white cloud of the image contributes substantially to the ablation of tissue as described herein. The white cloud comprises a plurality of cavitation regions. When pressurized liquid comprising water is injected into water, small cavitations are generated in areas of low pressure in the shear layer, near the nozzle exit. The small cavitations may comprise cavitation vortices. The cavitation vortices merge with one another, forming large discrete cavitation structures that appear in the high speed images as cavitation clouds. These cavitation clouds provide effective ablation when interacting with tissue. Without being bound by any particular theory, it is believed that the cavitation clouds striking tissue cause substantial erosion of tissue related to the cavitations in combination with the high velocity fluid that defines the cavitation clouds striking tissue.

The nozzle and pressure as described herein can be configured to provide the pulsatile clouds, for example with control of the angle of the nozzle, by a person of ordinary skill on the art based on the teachings provided herein. In many embodiments, the nozzle of the fluid delivery element comprises a cavitating jet in order to improve ablation of tissue.

The fluid delivery element nozzle and pressure can be arranged to provide a shedding frequency suitable for removal of tissue. The fluid delivery element can be located on the probe at a distance from the tissue as described herein in order to provide improved tissue resection.

In many embodiments, the "white cloud" of "flame" comprises an "entrainment" region where surrounding water is drawn in or "entrained" into the jet. Work in relation to embodiments suggests that the entrainment of fluid can be related to the shedding frequency.

The shedding frequency and size of the cloud shed from the jet can be used to provide tissue ablation in accordance with embodiments. The shedding frequency can be combined with the angular sweep rate of the probe around the longitudinal axis to provide overlap of the locations where each cloud interacts with the tissue.

The shedding pulses as described herein can be beneficially combined with the scanning of the jet as described herein.

Figure 4:
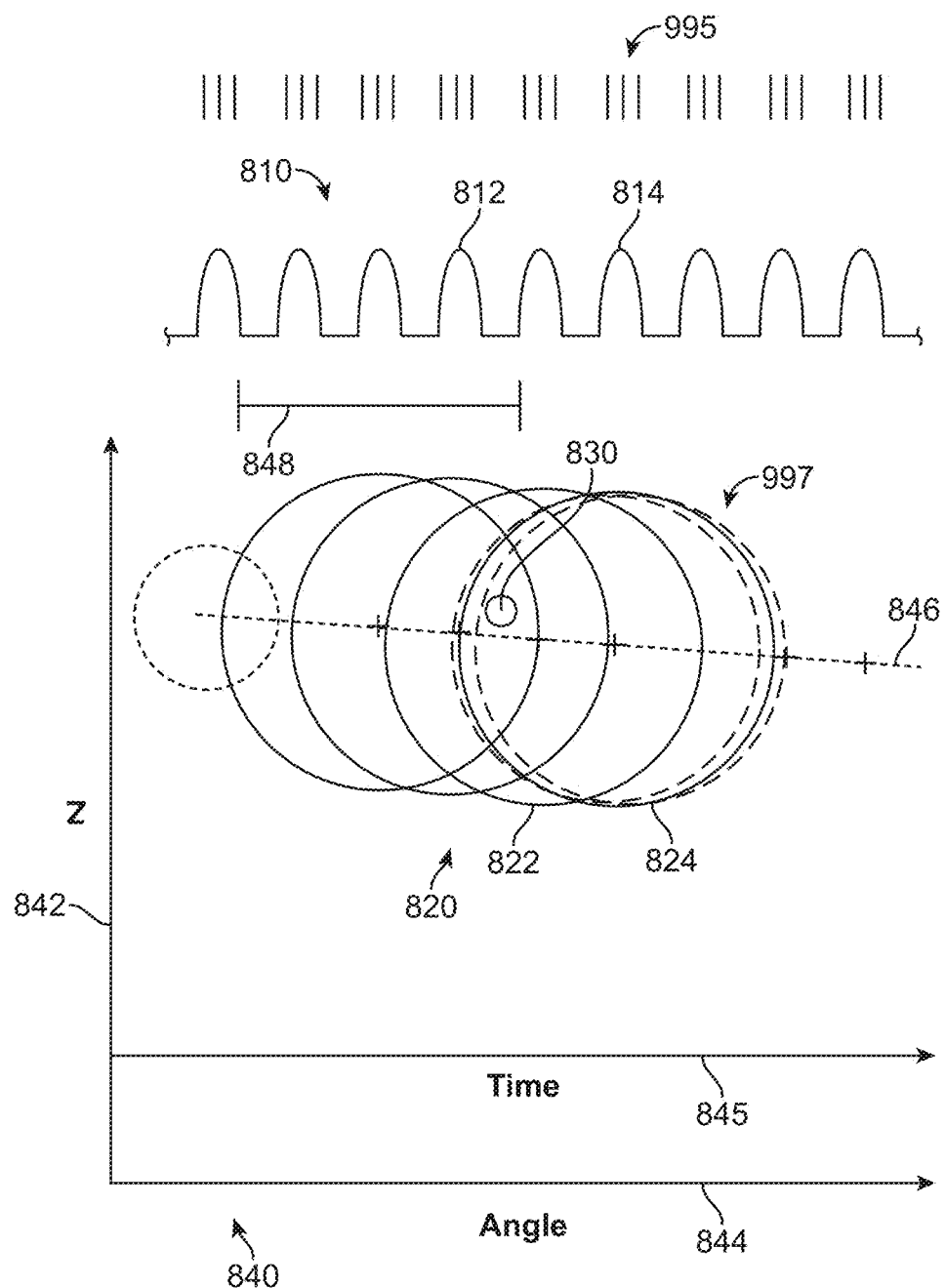
FIG. 4 shows a plurality of shedding pulses 995 and sweeping of the ablative jet to provide smooth and controlled tissue erosion at a plurality of overlapping locations 997 in accordance with embodiments.

FIG. 4 shows a plurality of shedding pulses 995 and sweeping of the ablative jet to provide smooth and controlled tissue erosion at a plurality of overlapping locations 997 in accordance with embodiments. This shedding frequency can be substantially faster than the pump frequency, when a pump is used, such that a plurality of shedding clouds are provided for each pulse of the pulsatile pump. The sweep rate of the probe can be related to shedding frequency to provide improved tissue removal, for example with the shedding clouds configured to provide overlapping pulses.

In many embodiments, the system comprises a pump having a frequency less than a frequency of the shedding pulses, in order to provide a plurality of shedding pulses for each pulse of the pump. The pump can have a pulse rate of at least about 50 Hz, for example within a range of about 50 Hz to about 200 Hz, and the shedding pulses comprise a frequency of at least about 500 Hz, for example within a range from about 1 kHz to about 10 kHz.

Although pulses of a pump are illustrated, similar scanning of pulsed clouds can be provided with a continuous flow pump.

While the nozzle can be configured in one or more of many ways, in many embodiments the nozzle comprises a Strouhal number (hereinafter "St") within a range from about 0.02 to about 0.3, for example within a range from about 0.10 to about 0.25, and in many embodiments within a range from about 0.14 to about 0.2.

In many embodiments, the Strouhal number is defined by:

$$St = (Fshed)*(W)/U$$

where Fshed is the shedding frequency, W is the width or diameter of the cavitating jet, and U is the velocity of the jet at the exit. A person of ordinary skill in the art can modify nozzles as described herein in order to obtain shedding frequencies suitable for combination in accordance with embodiments described herein, and experiments can be conducted to determine the cloud lengths and shedding frequencies suitable for tissue removal.

The nozzle configurations providing plurality of shedding clouds are suitable for use with one or more of the treatment probes as described herein.

Cavitation

Cavitation is a phenomenon that occurs when a high-pressure waterjet shoots through a nozzle into a liquid medium. Localized vapor pockets form as nuclei containing minute amounts of vapor and/or gas destabilize as they are subjected to drops in pressure rather than the commonly known method of addition of heat. Cavitation occurs when the local pressure drops below the vapor pressure, which occurs when the negative pressure coefficient (−Cp) is greater than cavitation number (a), respectively governed by the equations below $$-C_p = \frac{p_{ref} - p}{\frac{1}{2}\rho v_{ref}^2} \quad (1)$$

$$\sigma = \frac{p_{ref} - p_v}{\frac{1}{2}\rho v_{ref}^2} \quad (2)$$

where $p_{ref}$ is the hydrostatic pressure at the nozzle depth, p is the local pressure at the jet, $\rho$ is the fluid density, $v_{ref}$ is the exit velocity of the waterjet at the nozzle, and $p_v$ is the vapor pressure. When a liquid flows through a constricted region, its velocity increases to maintain continuity and there is a corresponding drop in pressure, known as the Venturi effect. Applying this to submerged waterjets, the velocity of water exiting through a nozzle is increased dramatically due to the constriction while the pressure of the jet stream is substantially reduced. When the pressure reduction is significant enough, it can drop below the vapor pressure, resulting in vapor cavity formation.

For a given flow dynamic, a cavitation number 6 exists above which cavitation does not occur and below which cavitation will be present with increased cavitating region size. Several smaller pockets can combine to form a larger vapor cavity. As the momentum of the waterjet carries the vapor cloud further away from the nozzle into surrounding medium, viscous forces cause the jet velocity to drop and there is a corresponding rise in pressure. This rise causes the vapor cavity to collapse, resulting in a pressure pulse which further accelerates nearby water and causes localized microjets to form. Both the liquid microjets and pressure pulse can exceed the damage threshold energy of a material and cause erosion. Due to the rapid loss in velocity as the jet moves away from the nozzle, beyond a given distance the kinetic energy of the stream no longer exceeds the threshold energy and pressure waves and microjets from collapsed cavitation clouds becomes the primary modality for erosion.

In many embodiments, cavitation is dependent on local changes in pressure only, making it an isothermal phenomenon, meaning no thermal fluctuations are expected. Experimentally, as the vapor cavitation grows in size, latent heat is drawn from the surrounding liquid, and a very small drop in temperature (~0.35° C.) can be observed. Although in many embodiments, the process is not entirely isothermal, the almost negligible change in temperature is why waterjet cutting is useful for machining sensitive parts that demand no heat-affected zones.

In many embodiments, pressure pulse and microjet erosion becoming the primary modality of material removal is the limited erosion radius. Since cavitation occurs due to the pressure differential of the waterjet relative to the ambient liquid pressure, vapor cavities can only exist up to a maximum distance before the cavity collapses as the jet slows down and the pressure comes to equilibrium with the surrounding liquid. As a result, submerged waterjet cutting becomes substantially self-limiting due to the range of pressure pulses and microjets before they dissipate and is a very safe and high precision tool to cut with. In alternative embodiments, a gaseous waterjet will have high kinetic energy levels that exceed the threshold energy at much longer distances since there are relatively minimal forces acting on the jet to slow it down.

Figure 5:
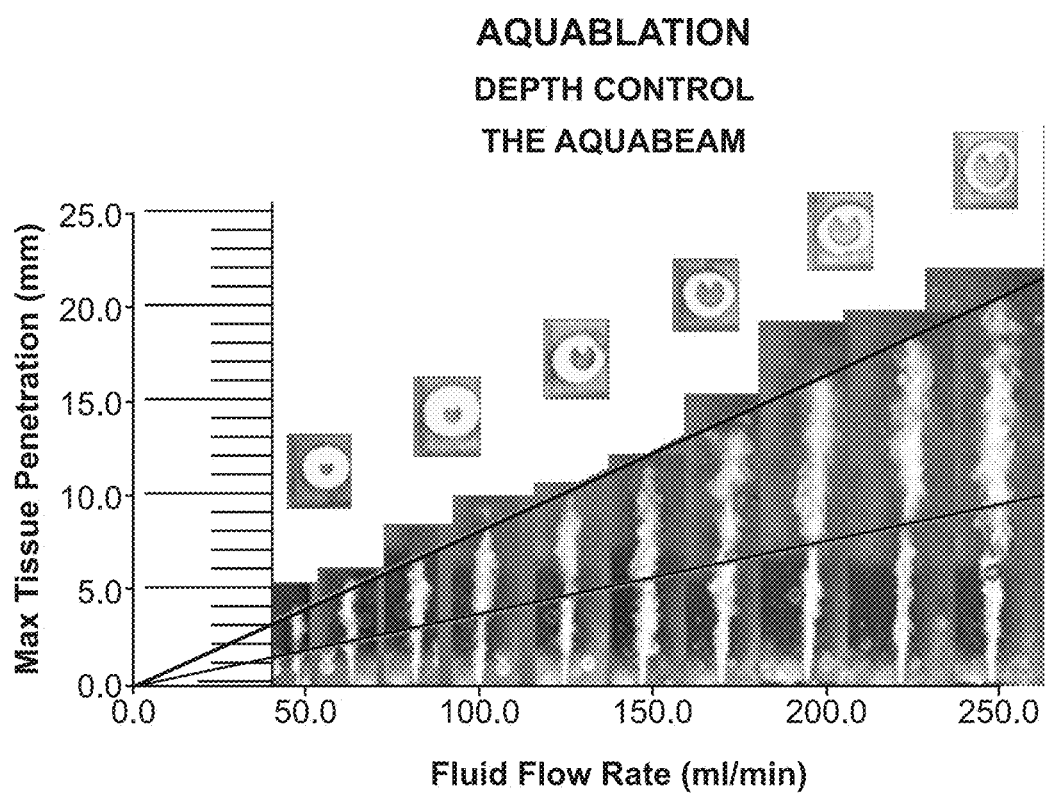
FIG. 5 shows maximum tissue penetration depth of cutting and flow rate through a nozzle in accordance with embodiments.

FIG. 5 shows maximum tissue penetration depth of cutting and flow rate through a nozzle in accordance with embodiments. The maximum penetration depth corresponds substantially to the length of the cavitation bubbles of the jet comprising the "cold" aquablation flame. The maximum tissue penetration depth of ablation corresponds directly to the flow rate and in many embodiments is linearly related to the flow rate.

The flame with cavitations is shown with 10 flow settings corresponding to flow rates within a range from about 50 ml/min to about 250 ml/min with a nozzle and rotating probe as described herein. The maximum penetration depth ranges from about 4 mm at 50 ml/min to about 20 mm at 250 ml/min.

The inset of FIG. 5 shows cut potato as a model of prostate BPH, in accordance with embodiments. The maximum penetration depth of potato corresponds closely to the maximum cut depth of BPH. The potato is shown cut with 6 flow settings corresponding to flow rates within a range from about 50 ml/min to about 250 ml/min with a nozzle and rotating probe as described herein. The maximum penetration depth ranges from about 4 mm at 50 ml/min to about 20 mm at 250 ml/min, consistent with the images of the cavitations of the jet comprising the cool "flame" as described herein.

In many embodiments, the cavitation cloud growth and length comprise a function of flow rate, which is proportional to the injection pressure and vice versa, for an appropriately configured nozzle as described herein. As the pressure increases, the maximum erosive radius appears to increase linearly, which is shown as the maximum penetration depth of FIG. 5.

High velocity cavitating jets can be created by using a known high-pressure pump to force the water through a nozzle in either a continuous or pulsatile flow. Despite the flow type produced by a pump, the cavitation phenomenon will be pulsatile due to the unsteady nature of vapor cavities and the cavity formation will be pulsatile even in a continuous flow jet as described herein. Without being bound to a particular theory, it is believed that both pulsatile and continuous flow waterjets will result in equivalent amounts of material erosion over a given amount of time. In many embodiments, nozzle geometry is configured to provide the flow dynamics and cavitation process as described herein. In many embodiments, the nozzle is configured to inhibit tight constriction at the waterjet exit, which can be related cavitation can occur inside the nozzle itself. In many embodiments, the sharp corners cause the water to separate from the wall and converge towards the nozzle centerline, further constricting the waterjet pathway while simultaneously reducing frictional effects caused by the nozzle wall. This results in an increased velocity along with the corresponding pressure drop and the vapor cavities formation. Vapor cavity formation will impact the overall flow dynamics as their eventual collapse results in turbulence and can affect erosion depth. A person of ordinary skill in the art can conduct experiments to determine appropriate nozzle geometry and flow rate to provide tissue removal as described herein without undue experimentation.

Aquablation

Submerged waterjet cutting as described herein has the capability to take advantage of the cavitation phenomenon to treat patients with Benign Prostatic Hyperplasia (BPH). The jet removes the excess soft tissue growth seen in BPH through the pressure pulses and microjets caused by collapsed vapor cavities. The waterjet direction can be manipulated by changing the location and orientation of the devices nozzle in one or more of many ways. For example, by one or more of translating the nozzle along the anterior-posterior direction or by rotating the nozzle up to an angle such as 180 degrees, for example, and combinations thereof. As the handpiece probe may sit on the anterior side of the prostate, a rotation angle can be used for ablating the tissue obstruction.

As vapor cavity formation and its erosive strength is a function of both injection pressure and the flow dynamics, the depth of material can be controlled by configuring the pressure as well as nozzle geometry. A greater injection pressure can result in a faster exit velocity. As described herein, the nozzle geometry can further increase the velocity depending on the constriction and will affect the degree of pressure drop as the waterjet exits through the Venturi effect. These factors can result in longer distances the cavitation clouds can grow to and travel before collapsing and releasing pressure pulses and microjets. The nozzle geometry and pressure settings of the Aquablation system have been optimized to give the user precise control and ensure the cavitating jet removes only the desired benign tissue growth.

The images provided herein show the how tissue erosion depth is a function of pressure, in accordance with embodiments. The images show the smaller cavitation cloud length and corresponding tissue resection depth for a lower injection pressure as compared with other images.

In many embodiments, Aquablation as described herein is capable of removing the excess tissue growth, e.g. BPH, with substantial removal and damage of arteries and veins and inhibited bleeding. In many embodiments, the jet is positioned to provide cavitation energy above the threshold of both growth tissue such as BPH and collagenous tissue such as blood vessels, with decreased bleeding. The pressure pulses and microjets provided by cavitation exceed the threshold energy required to erode the soft tissue growth and the other structures like vessels which have a much higher threshold energy.

In many embodiments, generation of harmful emboli are inhibited. Vapor cavity formation may benefit from a minute nucleus of air already present in the blood stream, for example. Cavitation can result in the growth of the nucleus without any additional air being introduced into the system. Furthermore, the cavity will collapse once the local jet pressure exceeds the vapor pressure, such that the air pockets may reduce back to their original nucleus size. In many embodiments, embolus formation is inhibited as cavitation depends on and can be limited to micro amounts of air native to the saline solution surrounding the urethra, and the vapor cavities quickly dissipate as the jet pressure begins to rise.

Figure 6:
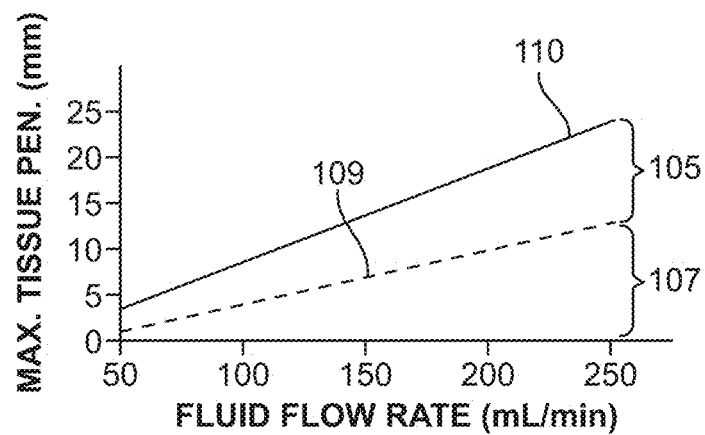
FIG. 6 shows maximum tissue penetration versus flow rate similar to FIG. 5 in accordance with embodiments.

FIG. 6 shows maximum tissue penetration 110 versus flow rate similar to FIG. 5 in accordance with embodiments. The nozzle positions in relation to tissue can be used to determine the tissue incision as substantially abrasive, or substantially selective, and combinations thereof, for example. Selective tissue removal 105 of substantially non-collagenous tissue such as BPH at rates substantially faster than collagenous tissue such as vessels can be provided at distances beyond a transition threshold 109. Highly abrasive substantially non-selective removal 107 can be provided at distances from tissue less than the threshold distance 109, for example. The transition threshold may comprise a substantially linear function with an offset. For example, the slope can be somewhat steeper than the transition threshold with an offset.

The threshold transition from selective tissue removal to highly abrasive substantially non-selective tissue removal may comprise one or more of many functions of flow rate and distance from the nozzle. For example, the threshold transition may comprise one or more of a linear function, a polynomial function, or an empirically determined transform function, and combinations thereof, for example. A person of ordinary skill in the art can determine the distances for selective removal and substantially abrasive tissue removal in accordance with the teachings as described herein without undue experimentation.

Figure 7:
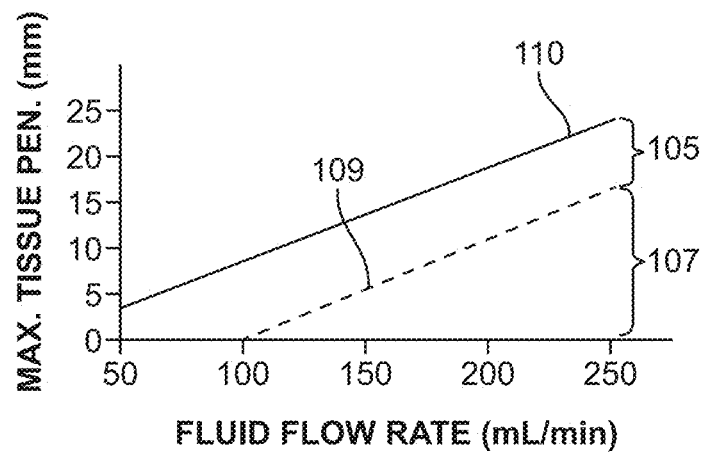
FIG. 7 shows a threshold transition from selective removal to abrasive removal comprising a slope similar to the slope of the maximum penetration depth, with an offset in accordance with embodiments.

FIG. 7 shows a threshold 109 transition from selective removal 105 to abrasive removal 107 comprising a slope similar to the slope of the maximum penetration depth 110, with an offset in accordance with embodiments. The offset can be related to the fluid jet parameters as described herein.

Figure 8A:
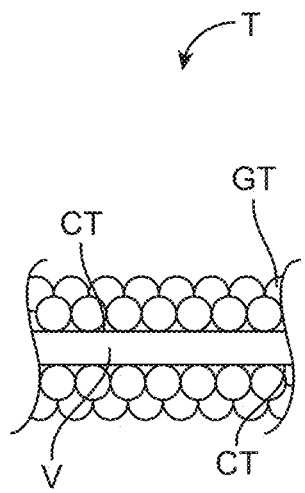
FIGS. 8A and 8B show selective tissue removal, in accordance with embodiments.
Figure 8B:
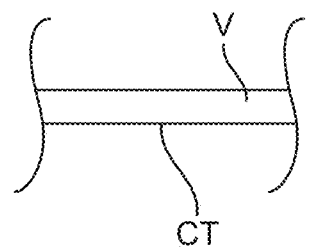

FIGS. 8A and 8B show selective tissue removal, in accordance with embodiments. The tissue can be positioned at a distance greater than the transition threshold in order to provide selective tissue removal. FIG. 8A shows tissue T prior to selective removal. The soft granular tissue GT can be substantially removed with inhibited removal of collagenous tissue CT such as blood vessels V, as shown in FIG. 8B. Work in relation to embodiments suggests that the shedding pulses as described herein can affect the endothelium, which may contribute to clotting and decreased bleeding in accordance with some embodiments.

Figure 9A:
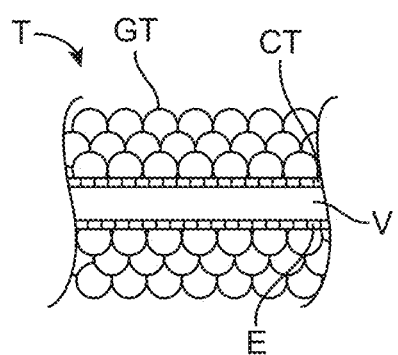
FIGS. 9A and 9B show highly abrasive tissue removal in accordance with embodiments.
Figure 9B:
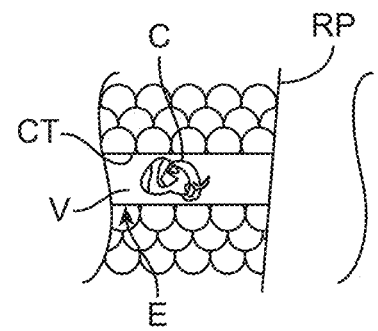

FIGS. 9A and 9B show highly abrasive tissue removal in accordance with embodiments. FIG. 9A shows tissue T prior to removal. FIG. 9B shows the tissue subsequent to removal. The collagenous tissue CT comprising the blood vessel V can be removed at substantially the same rate as the substantially less collagenous granular tissue GT such as BPH, as shown with the removal profile RP. The highly abrasive tissue removal can be provided with the nozzle positioned at a distance less than the transition threshold for a provided flow rate as described herein.

In many embodiments, the endothelial cell lining E of the blood vessels V can be affected so as to provide one or more of micro clotting; clotting; emboli or micro-emboli, and one or more biological responses as described herein. In many embodiments, induced micro-clotting C can substantially occlude the blood vessels and capillaries of the occluded tissue.

Figure 10:
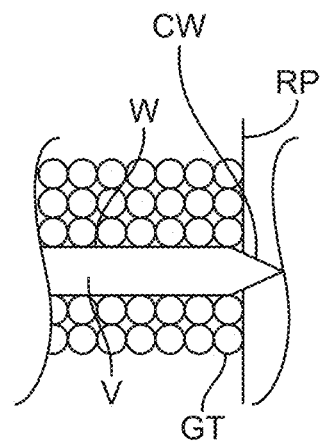
FIG. 10 shows a collapsed vessel wall, in accordance with embodiments.

FIG. 10 shows a collapsed vessel wall CW, in accordance with embodiments. The collapsed vessel wall CW can be generated with the highly abrasive cavitation as described herein. In many embodiments, the cavitation and jet can induce collapse of the vessel wall W. The collapse of the vessel wall can inhibit blood flow through the incised end of the vessel V.

The vessel wall can inhibit blood flow in one or more of many ways in response to the cavitation. In many embodiments, the ends of the cut vessel may comprise strands of cut collagen that provide an increased surface area to provide interaction with platelets and blood cells to induce clotting. The frayed ends of the blood vessel can extend inwardly toward to the end of the severed blood vessel so as to inhibit bleeding, for example. Alternatively or in combination, the endothelium of the blood vessel can be affected so as to provide clotting within the vessel.

Figure 11A:
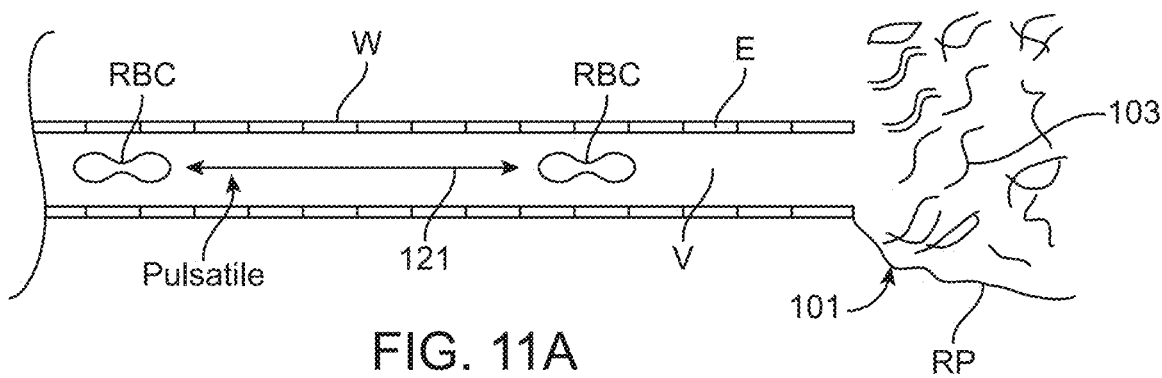
FIG. 11A shows a water jet flame removing tissue with shedding pulses in accordance with embodiments.

FIG. 11A shows a water jet flame 101 removing tissue with shedding pulses in accordance with embodiments. In many embodiments, the water shedding pulses induce a shear wave 121 along the lumen of the blood vessel V. The plurality shedding pulses as described herein can provide oscillations of the liquid within the blood vessel. In many embodiments, the oscillations provide a shear wave propagating transverse to the vessel wall W at a distance from the tissue region where the flame strikes. This shear wave can induce coagulation at a distance from the region contacted with the cavitation 103 as shown in FIG. 11A. The disruption of the vessel at a distance from the jet may comprise one or more of shearing of the endothelial layer E of the vessel, lysis of a plurality of endothelial cells at a distance, shearing of a plurality of red blood cells RBC, lysis of the plurality of red blood cells shearing of platelets, partial removal of endothelial cells from the vascular wall, complete removal of endothelial cells, generation of fibrin or clotting, and combinations thereof, for example.

In many embodiments, the plurality of shedding pulses comprises at least about two shedding pulses for each pulse of the pump, for example within a range from about 5 to about 20 shedding pulses per pulse of the pump. The shedding pulses may comprise highly abrasive shedding pulses as described herein, or selective shedding pulses as described herein, and combinations thereof for example.

Work in relation to embodiments suggests that the substantially abrasive zone of the jet comprising shedding pulses can be effective in providing the increased clotting as described herein. Alternatively or in combination, the selective tissue removal zone can be effective in providing the increased clotting as described herein.

Figure 11B:
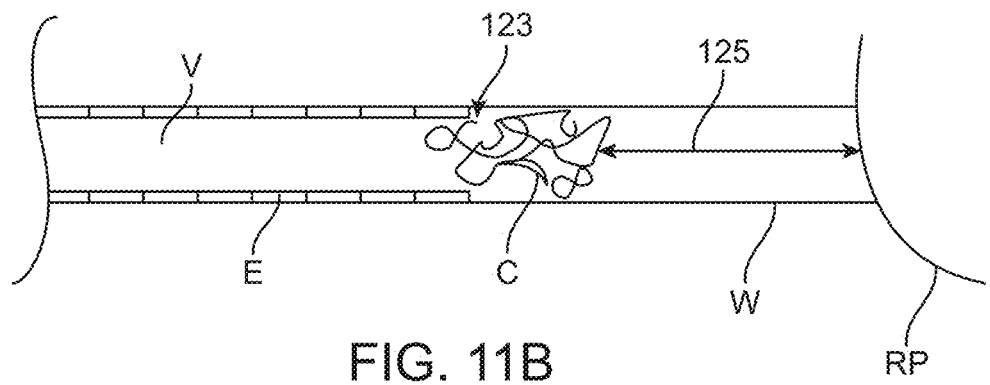
FIG. 11B shows disruption to a blood vessel in accordance with embodiments.

FIG. 11B shows disruption 123 to a blood vessel V in accordance with embodiments. The disruption of the endothelium E and corresponding clotting C as described herein are shown at a distance 125 from the tissue removal profile RP.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof

What is claimed is:

1. An apparatus to ablate vascular tissue, the apparatus comprising,
a pump;
a nozzle coupled to the pump, the nozzle sized for immersion in a liquid; and
circuitry coupled to the pump and the nozzle, the circuitry configured to provide a plurality of shedding pulses with a jet released into the liquid, the plurality of shedding pulses providing a pulsatile shear wave.

2. The apparatus of claim 1, wherein the pump provides a flow rate and the nozzle is configured to provide the plurality of shedding pulses in order to provide the pulsatile shear wave extending a distance from a cut profile to an affected location of a blood vessel, and wherein the affected location promotes blood clotting.

3. The apparatus of claim 1, wherein the nozzle is configured to be arranged with the tissue at a distance no more than a threshold transition distance from the tissue.

4. The apparatus of claim 1, wherein the nozzle is configured to be arranged with the tissue at a distance greater than a threshold transition distance from the tissue.

5. The apparatus of claim 1, further comprising a processor comprising instructions to treat the vascular tissue with the nozzle, the processor coupled to a linkage to move the nozzle in response to the instructions, wherein the processor comprises instructions to remove the tissue with a tissue removal profile with the nozzle positioned at a distance no more than a threshold transition distance for selective tissue removal from the tissue removal profile.

6. The apparatus of claim 1, wherein the pump comprises a piston to deliver a plurality of pump pulses and wherein the nozzle and a flow rate of the pump are configured to provide a plurality of pump pulses and each of the plurality of pump pulses provides a plurality of shedding pulses.

7. The apparatus of claim 1, further comprising a processor comprising instructions to treat the vascular tissue with the nozzle, the processor coupled to a linkage to move the nozzle in response to the instructions, wherein the processor comprises instructions to remove the tissue with a tissue removal profile with the nozzle positioned at a distance no more than a threshold transition distance from the tissue removal profile for selective tissue removal.

8. The apparatus of claim 1, wherein the nozzle is configured to be arranged to be directed toward tissue to be cut, wherein jet hydrodynamic parameters are configured to allow mechanical disruption of the tissue, and wherein the jet hydrodynamic parameters are also configured to inhibit bleeding.

9. The apparatus of claim 8, wherein the jet hydrodynamic parameters comprise one or more of a fluid jet velocity or a shear stress field, and/or wherein the jet hydrodynamic parameters are configured to control a cavitation field in order to cut the tissue with inhibited bleeding.

10. The apparatus of claim 1, wherein the nozzle is configured to provide the jet and is directed toward the vascular tissue in the liquid to cut said tissue through mechanical interaction of the jet with the tissue, wherein bleeding of cut vessels within the tissue is inhibited by one or more of platelet aggregation or thrombus formation in response to one or more hydrodynamic parameters of the jet.

11. The apparatus of claim 1, wherein the pulsatile shear wave extends a distance from a tissue removal profile to an affected location of a blood vessel, and wherein the pulsatile shear wave promotes hemostasis at the affected location.

12. The apparatus of claim 1, wherein the jet comprises a substantially abrasive jet in order to remove vessels and non-vascular tissue of the vascular tissue at similar rates, and/or wherein the plurality of shedding pulses comprises substantially abrasive shedding pulses in order to remove vessels and non-vascular tissue of the vascular tissue at similar rates.

13. The apparatus of claim 1, wherein the plurality of shedding pulses is configured to remove the vascular tissue along a removal profile and further configured to decrease bleeding at a distance from the removal profile.

14. The apparatus of claim 13, wherein the plurality of shedding pulses is configured to decrease the bleeding of the vascular tissue with one or more of induced thrombosis in capillaries and arterioles related to endothelial injury, shear stress and reduction in blood flow, adhesion and aggregation of platelets, deposition of fibrin, deposition of fibrin related to obstructive vessel clotting, fluid pressure in an affected zone, fluid pressure in an affected zone at a distance from the removal profile, inhibited blood flow in affected blood vessels, partial collapse of the affected blood vessels, or full collapse of the affected blood vessels.

* * * * *